United States Patent
Gresham

(10) Patent No.: US 8,133,174 B2
(45) Date of Patent: Mar. 13, 2012

(54) SELF CONSTRICTING ORIFICE SEAL

(75) Inventor: Richard D. Gresham, Guilford, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 907 days.

(21) Appl. No.: 12/124,479

(22) Filed: May 21, 2008

(65) Prior Publication Data

US 2008/0300466 A1    Dec. 4, 2008

Related U.S. Application Data

(60) Provisional application No. 60/932,330, filed on May 30, 2007.

(51) Int. Cl.
*A61B 1/32* (2006.01)
(52) U.S. Cl. ........................................ 600/206; 600/114
(58) Field of Classification Search .......... 600/201–246, 600/114, 108
See application file for complete search history.

(56) References Cited

U.S. PATENT DOCUMENTS

| | | | |
|---|---|---|---|
| 4,978,341 A | 12/1990 | Niederhauser | |
| 5,030,206 A | 7/1991 | Lander | |
| 5,053,016 A | 10/1991 | Lander | |
| 5,059,186 A | 10/1991 | Yammamoto et al. | |
| 5,108,380 A | 4/1992 | Herlitze et al. | |
| 5,263,944 A | 11/1993 | Vidal et al. | |
| 5,304,143 A | 4/1994 | Green et al. | |
| 5,308,336 A | 5/1994 | Hart et al. | |
| 5,334,164 A | 8/1994 | Guy et al. | |
| 5,342,315 A | 8/1994 | Rowe | |
| 5,366,445 A | 11/1994 | Haber | |
| 5,385,552 A | 1/1995 | Haber | |
| 5,385,553 A | 1/1995 | Hart | |
| 5,389,081 A | 2/1995 | Castro | |
| 5,391,153 A | 2/1995 | Haber | |
| 5,391,154 A | 2/1995 | Young | |
| 5,397,314 A | 3/1995 | Farley | |
| 5,407,433 A | 4/1995 | Loomas | |
| 5,411,483 A | 5/1995 | Loomas | |
| 5,417,705 A | 5/1995 | Haber | |
| 5,429,609 A | 7/1995 | Yoon | |
| 5,441,486 A | 8/1995 | Yoon | |
| 5,496,280 A | 3/1996 | Vandenbroek | |

(Continued)

FOREIGN PATENT DOCUMENTS

WO    WO 96/23536    8/1996

OTHER PUBLICATIONS

European Search Report dated Sep. 4, 2008, Application No. EP 08 25 1851.

(Continued)

*Primary Examiner* — Eduardo C Robert
*Assistant Examiner* — James Palmer

(57) ABSTRACT

An apparatus is disclosed for the reception of a surgical instrument inserted through a cannula assembly. An orifice in a seal member defines a central longitudinal axis in general alignment with the cannula assembly. The seal member includes an elastic member for engaging the surgical object about the orifice and forming a fluid-tight interface. A fiber loop is at least partially embedded in the elastic member and serves to compress central portions of the elastic member around the instrument. The fiber loop may form a loop around the orifice and may cooperate with other fiber loops similarly embedded in the seal.

16 Claims, 4 Drawing Sheets

U.S. PATENT DOCUMENTS

| | | |
|---|---|---|
| 5,538,509 A | 7/1996 | Dunlap |
| 5,545,142 A | 8/1996 | Stephens |
| 5,549,565 A | 8/1996 | Ryan |
| 5,603,702 A | 2/1997 | Smith |
| 5,634,908 A | 6/1997 | Loomas |
| 5,657,963 A | 8/1997 | Hinchliffe |
| 5,685,854 A | 11/1997 | Green |
| 5,709,664 A | 1/1998 | Vandenbroek |
| 5,720,759 A | 2/1998 | Green |
| 5,792,113 A | 8/1998 | Kramer |
| 5,814,026 A | 9/1998 | Yoon |
| 5,827,228 A | 10/1998 | Rowe |
| 5,895,377 A | 4/1999 | Smith |
| 5,913,847 A | 6/1999 | Yoon |
| 5,989,233 A | 11/1999 | Yoon |
| RE36,702 E | 5/2000 | Green |
| 6,083,203 A | 7/2000 | Yoon |
| 6,099,505 A | 8/2000 | Ryan |
| 6,171,299 B1 | 1/2001 | Bonutti |
| 6,358,266 B1 | 3/2002 | Bonutti |
| 6,482,181 B1 | 11/2002 | Racenet |
| 6,551,282 B1 | 4/2003 | Exline |
| 6,578,577 B2 * | 6/2003 | Bonadio et al. ............... 128/850 |
| 6,595,946 B1 | 7/2003 | Pasqualucci |
| 6,702,787 B2 | 3/2004 | Racenet |
| 6,811,546 B1 | 11/2004 | Callas |
| 6,923,783 B2 | 8/2005 | Pasqualucci |
| 6,942,671 B1 | 9/2005 | Smith |
| 7,011,314 B2 | 3/2006 | McFarlane |
| 7,025,747 B2 | 4/2006 | Smith |
| 7,083,626 B2 | 8/2006 | Hart |
| 7,169,130 B2 | 1/2007 | Exline |
| 7,244,244 B2 | 7/2007 | Racenet |
| 7,276,075 B1 | 10/2007 | Callas |
| 7,390,317 B2 | 6/2008 | Taylor |
| 7,438,702 B2 | 10/2008 | Hart |
| 7,470,255 B2 | 12/2008 | Stearns |
| 2001/0041872 A1 | 11/2001 | Paul |
| 2003/0187397 A1 | 10/2003 | Vitali |
| 2004/0054353 A1 * | 3/2004 | Taylor ............................. 606/1 |
| 2005/0155611 A1 * | 7/2005 | Vaugh et al. .................. 128/887 |
| 2010/0228093 A1 * | 9/2010 | Voegele et al. ............... 600/204 |

OTHER PUBLICATIONS

US 7,282,043, 10/2007, Racent (withdrawn)

\* cited by examiner

SELF CONSTRICTING ORIFICE SEAL

CROSS REFERENCE TO RELATED APPLICATION

The present application claims the benefit of and priority to U.S. Provisional Application Ser. No. 60/932,330 filed on May 30, 2007, the entire contents of which are incorporated herein by reference.

BACKGROUND

1. Technical Field

The present disclosure relates generally to a portal apparatus employing a seal for maintaining a fluid-tight connection with a surgical instrument. In particular, the disclosure relates to a portal apparatus employing a seal adapted to expediently deform upon insertion of the instrument.

2. Background of Related Art

Surgical procedures such as laparoscopic, arthroscopic, and endoscopic procedures in general are termed minimally invasive at least in part because the incision required is relatively small, perhaps one inch in length or less. Small incisions are preferred because they are inherently less traumatic to the body tissue. Also, small incisions only subject internal organs to a minimum of exposure to the contaminants in the outside atmosphere. Thus, small incisions enable shorter hospital stays and faster recoveries with less pain and scarring than is common with the larger incisions required for conventional surgery.

Endoscopic surgery is possible due in part to the availability of instruments designed specifically for this purpose. A cannula, for example, is an elongated tube, typically 5 mm to 13 mm in diameter, which may be configured to have a distal end inserted through the small incision to provide a working conduit to an internal body cavity adjacent an operative site. The body cavity is often inflated with an insufflation gas, carbon dioxide for example, to separate the body wall from vital organs. This provides a space where a surgeon may introduce viewing equipment or maneuver tools into position without damaging surrounding tissue. Various other instruments may then be inserted and withdrawn through the cannula for access to the working space and operative site. In order to fit through a cannula and also to enable a surgeon to manipulate tissue far removed from the incision, instruments adapted for endoscopic surgery typically include a long and narrow cylindrical shaft. A tool on the distal end of the shaft may be inserted through the cannula and positioned within the body near the operative site, while a working head at the proximal end of the shaft remains in the outside environment to be handled by a surgeon to control the tool.

Endoscopic procedures generally require that any instrumentation inserted into the patient's body be sealed, i.e. provisions must be made to ensure insufflation gasses, blood and other fluids do not escape the body through the cannula. Furthermore, a seal acts to prevent contamination of the body cavity by the outside environment. In the absence of such a fluid-tight seal, many of the attendant advantages of minimally invasive surgery are lost. Cannulas are often provided with a washer-shaped ring of a flexible material, such as an elastomer, sized so as to accommodate the cylindrical shaft of a surgical instrument. An orifice through the seal material can be sized just smaller than the instrument to be inserted so that a central portion of the seal material is displaced by the instrument and maintains contact with the shaft. The quality of the seal created depends in part on the amount of seal material contacting the shaft. Leakage of air and insufflation gasses might occur if the amount of contacting material is insufficient. Accordingly, a need exists for a cannula with a seal capable of providing a robust engagement with an instrument.

SUMMARY

The present disclosure describes a surgical portal apparatus which permits a surgical instrument to access a tissue site while maintaining a seal about the instrument. The portal apparatus includes a portal member dimensioned for positioning within body tissue with a passageway providing access to the tissue site, and a portal seal mounted in the passageway. The portal seal includes an elastic member with a passage generally along a seal axis that can deform to establish a substantial sealed relationship with the surgical instrument, and at least one fiber loop at least partially embedded within the elastic member. The fiber loop includes an inner loop portion at least partially circumscribing the passage, which is subject to an outward radial displacement upon insertion of the surgical object into the passage, and an outer loop portion that is drawn radially inward during the outward radial displacement of the inner loop portion. In this way, the fiber loop may be adapted to compress a central portion of the elastic member around the surgical object upon the inward radial displacement of the outer loop portion. The fiber loop may be formed from a flexible narrow strand of a substantially inelastic material, and may be arranged to substantially encircle the passage forming a loop structure positioned off-center with respect to the seal axis. The fiber loop may form a continuous loop member and the portal seal may include first and second fiber loops arranged such that inner loop portions of the respective fiber loops are at least partially overlapping. The first and second fiber loops may be arranged in a general diametrically opposed relation and may be accompanied by another pair of first and second fiber loops.

In another embodiment, the portal apparatus includes a seal having an elastic member with an orifice permitting passage of a surgical instrument along a seal axis, and a plurality of fiber loops at least partially embedded in the elastic member arranged such that respective inner loop portions of the fiber loops at least partially circumscribe the orifice and outer loop portions are relatively displaced from the seal axis. Upon insertion of a surgical object into the orifice, the inner loop portions are radially displaced causing a corresponding radially inward movement of the outer loop portions to draw the elastic member about the surgical instrument to establish a substantial sealed relationship. The seal may be characterized as a septum seal having a generally planar configuration. At least one fiber loop may protrude longitudinally from a general plane defined by the septum seal such that a longitudinal displacement of an inner portion of the fiber loop corresponds to an inward radial displacement of an outer portion of the fiber loop.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF PREFERRED EMBODIMENTS

Figure 1:
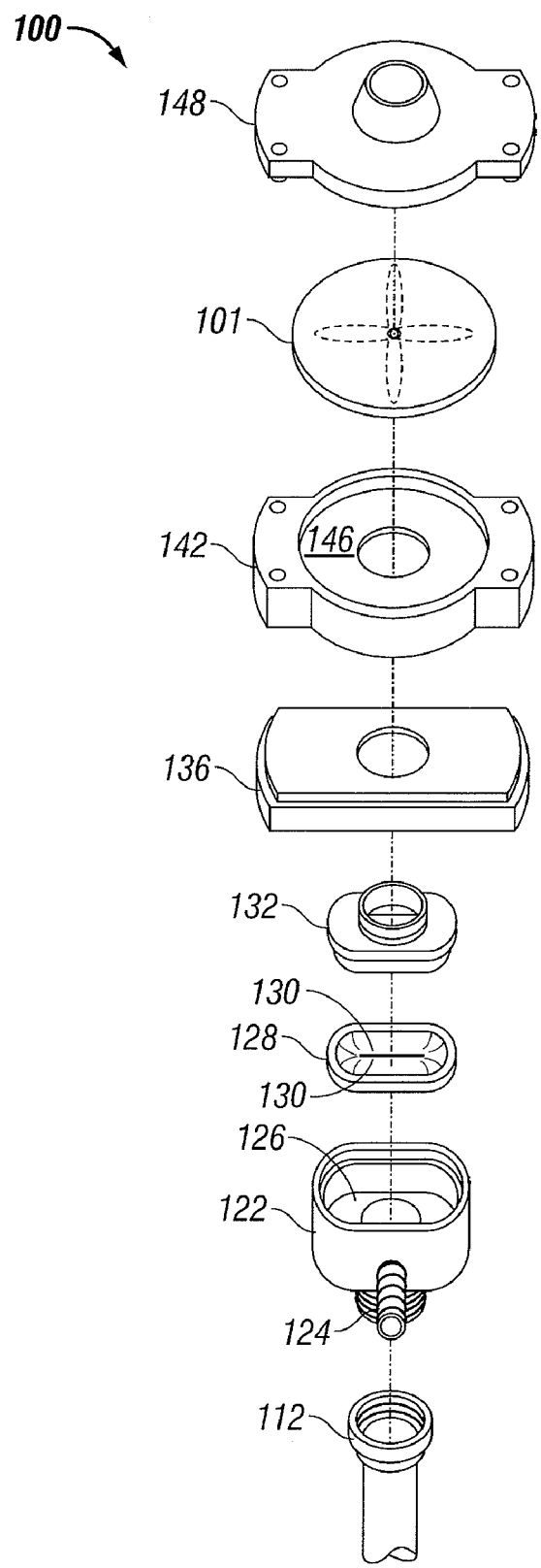
FIG. 1 is an exploded perspective view of a cannula assembly incorporating a self constricting orifice seal in accordance with the present disclosure.

The present disclosure contemplates the introduction into a person's body of all types of surgical instruments including clip appliers, graspers, dissectors, retractors, staplers, laser fibers, photographic devices, endoscopes and laparoscopes, tubes, and the like. All such objects are referred to herein generally as "instruments." In the drawings and in the description which follows, the term "proximal," as is traditional, will refer to the direction toward the operator or a relative position on the surgical device or instrument which is closer to the operator, while the term "distal" will refer to the direction away from the operator or relative position of the instrument which is further from the operator.

Referring initially to FIG. 1, cannula assembly 100 is a surgical portal apparatus including a portal seal such as self constricting orifice seal 101. At the distal most end of cannula assembly 100 is a portal member such as cannula 112. Cannula 112 is a hollow tube configured to connect to seal body 122 in a fluid-tight manner. Port 124 provides a conduit between a cavity 126 on the interior of seal body 122 and the outside environment. Lip seal 128 is an elastic member adapted to bias two distally extending lips 130 into a sealing engagement with one another. Lip seal 128 rests within cavity 126 of seal body 122 and is enclosed therein by snap cap 132. Adapter 136 connects snap cap 132 to lower housing 142. A circular opening 146 is disposed on the proximal end of lower housing 142. Self constricting orifice seal 101 is positioned within circular opening 146 and enclosed by the connection of upper housing 148 to lower housing 142 by any conventional means. Each component of cannula assembly 100, with the exception of lip seal 128, includes a central passageway extending from the proximal to distal end in general alignment with a central longitudinal axis.

In operation, a distal end (not shown) of cannula 112 is inserted through a small incision made in the body wall of a patient and positioned within a body cavity in the vicinity of an operative site. The proximal end of cannula 112 remains on an exterior side of the body wall. An insufflation gas may then be inserted through port 124 and directed distally through cannula 112 into the body cavity. At this point, with no instrument in use, lip seal 128 functions as a zero closure valve or seal preventing insufflation gasses from traveling proximally. When a surgical instrument is introduced to cannula assembly 100, it may be inserted first through upper housing 148. As the surgeon advances the instrument distally, the instrument encounters self constricting orifice seal 101, which creates a fluid-tight connection with the shaft of the instrument as will be described in detail below. The instrument may pass freely though lower housing 142, adapter 136, and snap cap 132 before encountering lip seal 128. The instrument separates lips 130 opening lip seal 128, and allowing insufflation gasses to travel proximally to self constricting orifice seal 101. At this point, with an instrument in place, it is the fluid-tight connection between the self constricting orifice seal 101 and the shaft of the instrument that prevents any further escape of insufflation gasses from cannula assembly 100. The fluid tight connection is maintained as the instrument is passed through seal body 122 and cannula 112 to the body cavity where it may be used to surgically manipulate tissue.

Figure 2A:
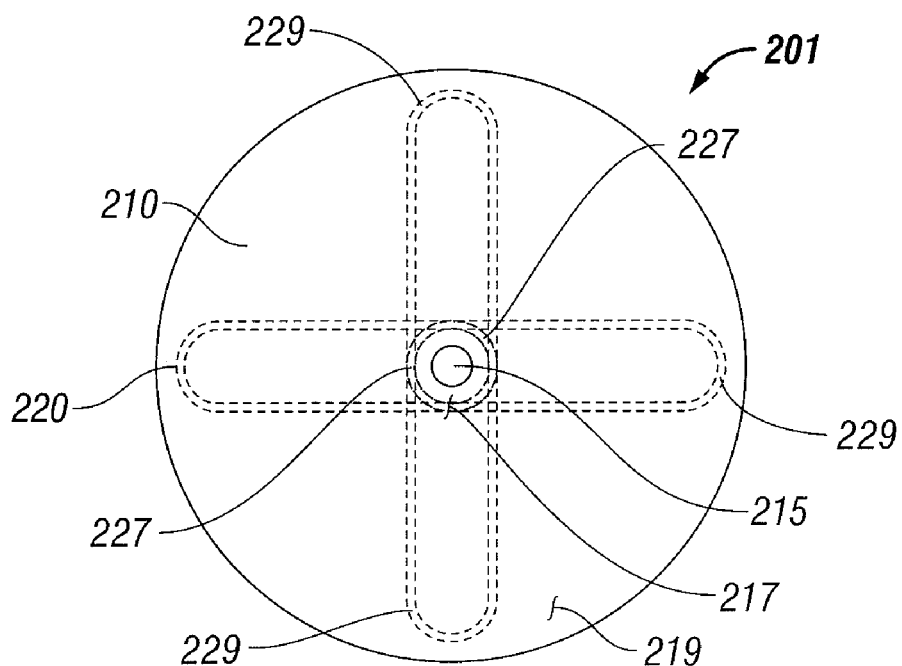
FIG. 2A is top view of the self constricting orifice seal of FIG. 1 in a relaxed condition.

Referring now to FIG. 2A, a self constricting orifice seal 201 will be described in detail. Self constricting orifice seal 201 may be characterized as a septum seal. Septum seals are defined generally as substantially planar elastomeric members having properties for radially compressing against the outer surface of an object. Self constricting orifice seal 201 includes two main components described below.

First, elastic member 210 is formed from an elastomeric material. Although a variety of materials may be appropriate, a low durometer polymer may be selected with a high degree of compliance to make it particularly adaptable to instruments of various sizes. A central orifice 215 extends through the elastic member 210 defining a seal axis and providing a passage for surgical instruments. Central orifice 215 is capable of expanding to accommodate an instrument inserted therethrough. Immediately surrounding central orifice 215 is the inner portion 217 of the elastic member. An outer portion 219 of the elastic member surrounds inner portion 217 and extends to the outside diameter of elastic member 210.

The second main component of self constricting orifice seal 201 is a set of fiber loops 220. Fiber loops 220 are at least partially embedded in elastic member 210 and may be embedded by any suitable means. A co-molding process such as insert molding may be employed whereby a first material is injected into a mold cavity and allowed to at least partially set to form the fiber loops 220, after which the mold cavity is modified to accommodate the second material to form the elastic member 210. Fiber loops 220 may be formed from any flexible material compatible with the elastic member 210 and may include natural or synthetic fibers such as plastic, rubber, glass, or metal. Fiber loops 220 may be substantially inelastic or have elastic properties, but should be less elastic than the elastic member 210 such that a force imparted on both components tends to stretch the fiber loops 220 less than the elastic member 210. As shown in FIG. 2A, fiber loops 220 may form continuous elongated loop members. Each oblong loop member is arranged in an off-center manner such that an inner loop portion 227 is centrally located within inner portion 217 and an outer loop portion 229 is located within outer portion 219 of elastic member 210. The fiber loops 220 substantially surround central orifice 215 and the seal axis defining loop structures.

Figure 2B:
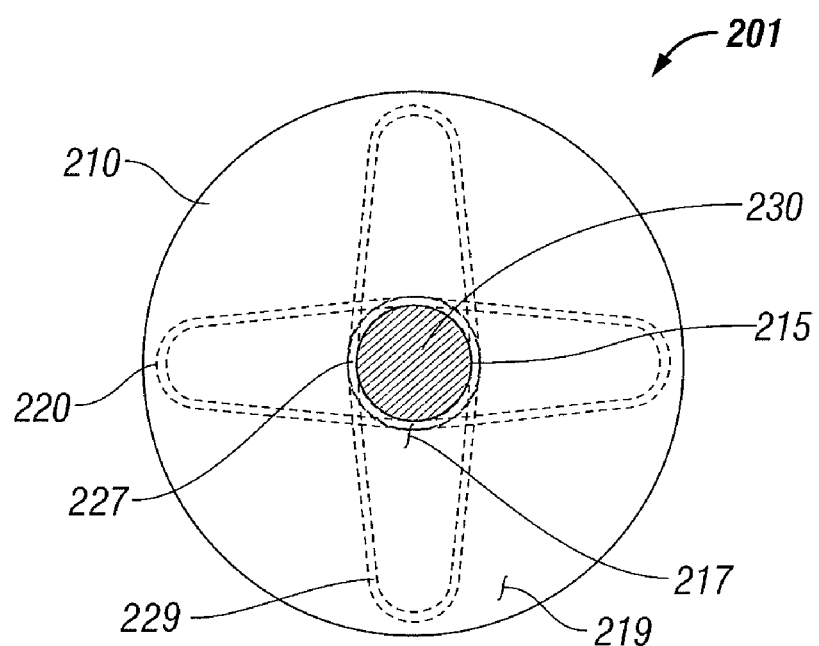
FIG. 2B is a top view of the self constricting orifice seal of FIG. 1 deformed to accommodate a surgical object.

Referring now to FIG. 2B, in operation, an instrument shaft 230 may be inserted through central orifice 215. To accommodate the instrument shaft 230, elastic member 210 deforms to expand central orifice 215, while fiber loops 220 will have a tendency to distort the shape of the loop structures. The inner loop portions 227 of fiber loops 220 are displaced radially outwardly, widening the loop structures in the vicinity of the central orifice 215. This widening creates tensile forces in the fiber loops 220 drawing outer loop portions 229 radially inward. The inward displacement outer loop portions 229 causes each loop structure to pull radially inward on the material in which it is embedded, including the outer portion 219 of elastic member 210. The inward pull causes more of the elastic material forming elastic member 210 to surround and contact instrument shaft 230. The increased amount of elastic material compressed around instrument shaft 230 along with inwardly directed forces imparted on the material by the fiber loops 220 establishes a snug fluid-tight connection to be made between elastic member 210 and instrument shaft 230.

Figure 3A:
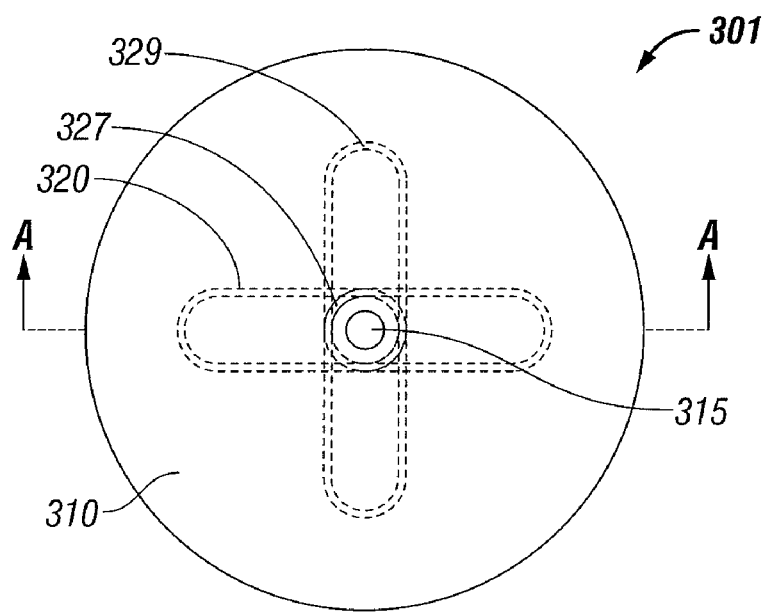
FIG. 3A is a plan view of a self constricting orifice seal having fully embedded fiber loops extending some distance from the orifice.
Figure 3B:
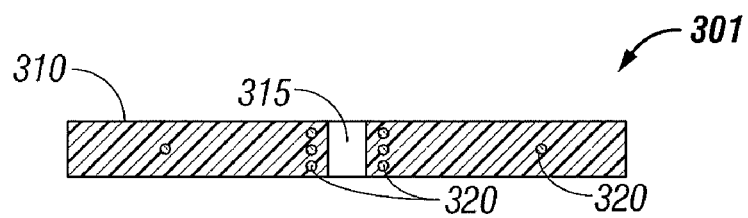
FIG. 3B is a cross-sectional view of the self constricting orifice seal taken along line A-A of FIG. 3A.

Referring now to FIG. 3A, self constricting orifice seal 301 includes two pairs of diametrically opposed fiber loops 320 fully embedded within elastic member 310. Again, each fiber loop 320 forms a loop structure surrounding central orifice 315, and defines a continuous loop member. Although the loop structures do not extend to the outer boundary of elastic member 310 as in the embodiment of FIGS. 2A and 2B, each loop is elongated such that the outer loop portions 329 are relatively displaced from the central orifice 315 and the corresponding seal axis in relation to the inner loop portion 327. In this way, the fiber loops 320 are adapted to draw in some part of elastic member 310 as an instrument deforms the shape of the loop structures. As can be seen in FIG. 3B, fiber loops 320 may form continuous loop members which are independent of one another, being spaced longitudinally within elastic member 310 in the regions of overlap near the orifice 315. Other embodiments may permit intersections of fiber loops.

Figure 4:
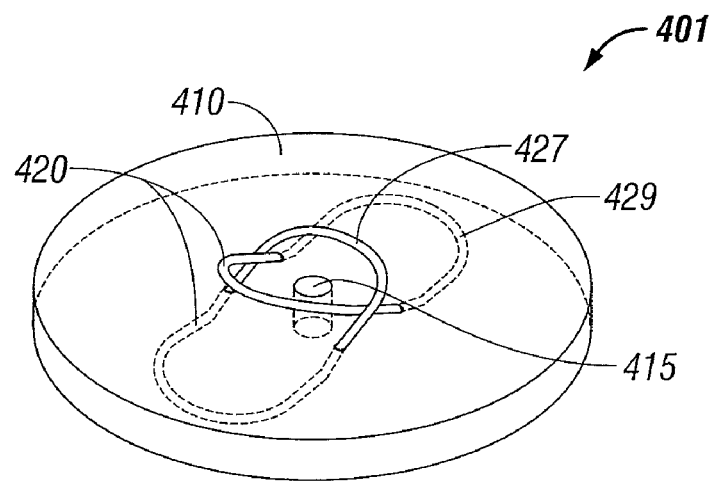
FIG. 4 is a perspective view of a self constricting orifice seal having partially embedded molded fiber loops.

Referring now to FIG. 4, an alternate embodiment of self constricting orifice seal 401 includes elastic member 410, central orifice 415, and molded fiber loops 420, which are partially embedded in elastic member 410. An inner loop portion 427 of molded fiber loop 420 protrudes longitudinally from elastic member 410 while an outer loop portion 429 is embedded. Molded fiber loops 420 are continuous loop members forming loop structures encircling the central orifice 415 and corresponding seal axis. Molded fiber loops 420 may act in the manner described above whereby a change in the width of the loop structures leads to portions of the elastic member 410 being drawn radially inward. Additionally, a longitudinal displacement of the inner loop portions 427 may contribute to an inward radial displacement of portions of the elastic member 410. If self constricting orifice seal 401 is oriented within a cannula assembly such that inner loop portions 427 protrude distally, an instrument may engage the inner loop portions 427 protruding from elastic member 410 drawing the inner loop portions 427 distally as the instrument is advanced toward an operative site. This longitudinal displacement of the inner loop portions 427 will create tension in fiber loops 420, which will have an inwardly directed radial component. Portions of the elastic member 410 surrounding embedded portions of fiber loops 420 will be drawn radially inward due to this radial component. This will compress the elastic member 410 around orifice 415 and an inserted surgical instrument.

Figure 5A:
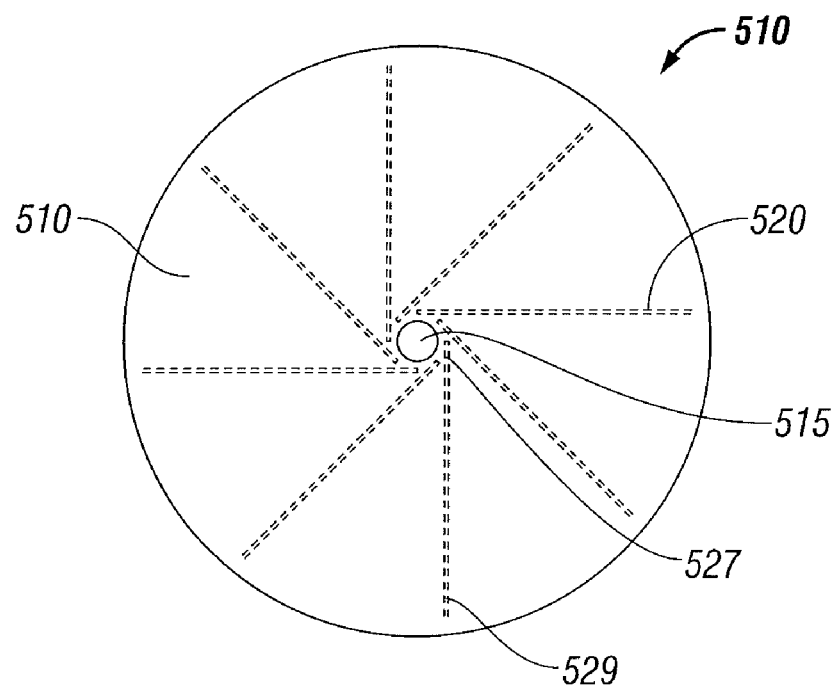
FIG. 5A is a plan view of a self constricting orifice seal having fiber loops embedded in a straight configuration.
Figure 5B:
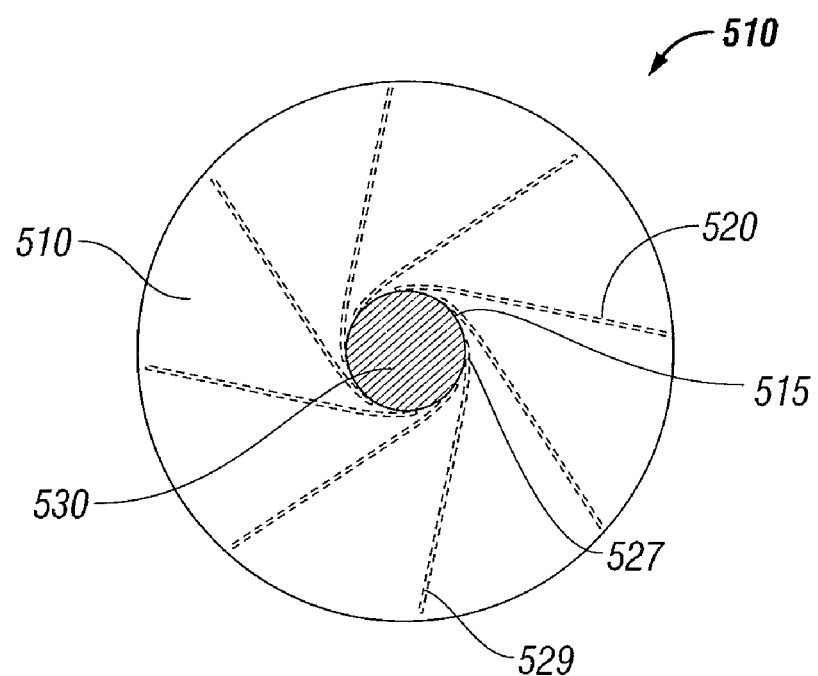
FIG. 5B is a plan view of the self constricting orifice seal of FIG. 5A deformed to accommodate a surgical object.

Referring next to the embodiment of FIG. 5A, self constricting orifice seal 501 includes elastic member 510, central orifice 515 and fiber members 520. Fiber members 520 include inner fiber portions 527 and outer fiber portions 529, and need not form continuous loop members to draw in elastic material of elastic member 510. As can be seen in FIG. 5B, upon the insertion of instrument shaft 530, inner fiber portions 527 of fiber members 520 are outwardly displaced. Being less elastic than elastic member 510, fiber members 520 tend to maintain their length by drawing outer fiber portions 529 radially inward to accommodate the outward displacement of the inner fiber portions 527. In this way, elastic member 510 is compressed about central orifice 515.

Although the foregoing disclosure has been described in some detail by way of illustration and example, for purposes of clarity or understanding, it will be obvious that certain changes and modifications may be practiced within the scope of the appended claims.

What is claimed is:

1. A surgical portal apparatus for permitting access to a tissue site, which comprises:
   a portal member dimensioned for positioning within body tissue, the portal member having a passageway providing access to a tissue site and to permit introduction of a surgical object used in performing a surgical procedure adjacent the tissue site; and
   a portal seal mounted relative to the portal member and defining a seal axis, the portal seal including an elastic member defining a passage to permit passage of the surgical object generally along the seal axis and being adapted to establish a substantial sealed relation with the surgical object, and at least one fiber loop at least partially embedded within the elastic member, the fiber loop including an inner loop portion at least partially circumscribing the passage and being subject to an outward radial displacement upon insertion of the surgical object into the passage and an outer loop portion subject to an inwardly radial displacement during the outward radial displacement of the inner loop portion.

2. The surgical portal apparatus according to claim 1 wherein the at least one fiber loop is adapted to compress the elastic member around the surgical object upon the inwardly radial displacement of the outer loop portion.

3. The surgical portal apparatus according to claim 2 wherein the at least one fiber loop comprises a flexible narrow strand of a substantially inelastic material.

4. The surgical portal apparatus according to claim 1 wherein the at least one fiber loop substantially encircles the passage defining a loop structure.

5. The surgical portal apparatus according to claim 4 wherein the loop structure is oblong and positioned off-center with respect to the seal axis.

6. The surgical portal apparatus according to claim 1 wherein the at least one fiber loop defines a continuous loop member.

7. The surgical portal apparatus according to claim 6 including first and second fiber loops arranged relative to the seal axis whereby the inner loop portions are at least partially overlapping.

8. The surgical portal apparatus according to claim 7 wherein the first and second fiber loops are arranged in a general diametrically opposed relation.

9. The surgical portal apparatus according to claim 8 including two pairs of first and second fiber loops.

10. A surgical portal apparatus for permitting access to a tissue site, which comprises:
    a portal member dimensioned for positioning within body tissue, the portal member having a passageway providing access to a tissue site and to permit introduction of a surgical object used in performing a surgical procedure adjacent the tissue site; and
    a portal seal mounted relative to the portal member and defining a seal axis, the portal seal including an elastic member defining an orifice to permit passage of the surgical object generally along the seal axis and a plurality of fiber loops at least partially embedded within the elastic member, the fiber loops arranged about the seal axis and having respective inner loop portions at least partially circumscribing the orifice and outer loop portions relatively displaced from the seal axis, the inner loop portions adapted to be radially displaced upon insertion of the surgical object to cause corresponding radially inward movement of the outer loop portions to draw the elastic member about the surgical object in substantial sealed relation therewith.

11. The surgical portal apparatus according to claim 10 wherein the elastic member is a septum seal, the elastic member defining a general seal plane.

12. The surgical portal apparatus according to claim 11 wherein at least one fiber loop is dimensioned to protrude longitudinally from the general seal plane.

13. The surgical portal apparatus according to claim 12 wherein the inner loop portion of the at least one fiber loop is subject to a longitudinal displacement upon insertion of the surgical object, the longitudinal displacement of the inner loop portion associated with a radially inward displacement of the outer loop portion of the at least one fiber loop.

14. The surgical portal apparatus according to claim 1, wherein the portal seal is a septum seal exhibiting a substantially planar configuration.

15. The surgical portal apparatus according to claim 14, wherein the elastic member defines an inner portion immediately surrounding the passage and an outer portion that radially surrounds the inner portion and extends to an outer periphery of the elastic member, and wherein the fiber loop extends substantially into both the inner and outer portions of the elastic member.

16. The surgical portal apparatus according to claim 1, wherein the fiber loop is fully embedded in the elastic member.

* * * * *